United States Patent [19]

Ryan

[11] Patent Number: 5,849,517

[45] Date of Patent: *Dec. 15, 1998

[54] METHOD AND COMPOSITION FOR PRESERVING ANTIGENS AND NUCLEIC ACIDS AND PROCESS FOR UTILIZING CYTOLOGICAL MATERIAL PRODUCED BY SAME

[75] Inventor: Wayne L. Ryan, Omaha, Nebr.

[73] Assignee: Streck Laboratories, Inc., Omaha, Nebr.

[ * ] Notice: The term of this patent shall not extend beyond the expiration date of Pat. Nos. 5,196, 182 and 5,459,073.

[21] Appl. No.: 682,926

[22] Filed: Jul. 16, 1996

Related U.S. Application Data

[60] Continuation-in-part of Ser. No. 603,740, Feb. 20, 1996, which is a division of Ser. No. 240,404, filed as PCT/US93/08520 Sep. 9, 1993, abandoned, which is a continuation-in-part of Ser. No. 943,359, Sep. 10, 1992, abandoned, which is a continuation-in-part of Ser. No. 877,738, May 4, 1992, Pat. No. 5,260,048, and Ser. No. 696,926, May 8, 1991, Pat. No. 5,196,182.

[51] Int. Cl.[6] .......................... G01N 31/00; G01N 33/50; C12Q 1/08; A01N 1/02

[52] U.S. Cl. ................. 435/40.51; 435/40.5; 435/40.52; 436/8; 436/16; 436/17; 436/18

[58] Field of Search .............................. 435/450.51, 40.5, 435/40.52; 436/16, 18, 17, 8

[56] References Cited

U.S. PATENT DOCUMENTS

| | | |
|---|---|---|
| 2,554,944 | 5/1951 | Ferrari . |
| 4,099,917 | 7/1978 | Kim . |
| 4,160,644 | 7/1979 | Ryan . |
| 4,219,440 | 8/1980 | Runck et al. . |
| 4,287,087 | 9/1981 | Brinkhous et al. . |
| 4,404,181 | 9/1983 | Mauthner . |
| 4,436,821 | 3/1984 | Ryan . |
| 4,493,821 | 1/1985 | Harrison . |
| 4,578,282 | 3/1986 | Harrison . |
| 4,652,449 | 3/1987 | Ropars et al. . |
| 4,666,699 | 5/1987 | Slifkin . |
| 4,704,364 | 11/1987 | Carver et al. . |
| 4,762,522 | 8/1988 | Maue . |
| 4,767,206 | 8/1988 | Schwartz . |
| 4,774,189 | 9/1988 | Schwartz . |
| 4,793,994 | 12/1988 | Helioff et al. . |
| 4,844,891 | 7/1989 | Rosent et al. . |
| 4,848,377 | 7/1989 | Bires et al. . |
| 4,867,908 | 9/1989 | Recktenwald et al. . |
| 4,876,189 | 10/1989 | Schetters et al. . |
| 4,880,602 | 11/1989 | Al-Sioufi . |
| 4,882,284 | 11/1989 | Kirchanski et al. . |
| 4,918,004 | 4/1990 | Schwartz . |
| 4,931,385 | 6/1990 | Block et al. . |
| 4,962,038 | 10/1990 | Carter et al. . |
| 4,980,176 | 12/1990 | Berke et al. . |
| 4,987,086 | 1/1991 | Brosnan et al. . |
| 5,008,201 | 4/1991 | Ryan . |
| 5,034,222 | 7/1991 | Kellett et al. . |
| 5,037,843 | 8/1991 | Schoenberg . |
| 5,059,518 | 10/1991 | Kortight et al. . |
| 5,073,623 | 12/1991 | Prantl et al. . |
| 5,091,174 | 2/1992 | Lemberger . |
| 5,106,744 | 4/1992 | Kass . |
| 5,112,871 | 5/1992 | Austin . |
| 5,118,173 | 6/1992 | Donofrio et al. . |
| 5,260,048 | 11/1993 | Ryan . |
| 5,262,327 | 11/1993 | Ryan . |
| 5,270,208 | 12/1993 | Ryan . |
| 5,300,424 | 4/1994 | Hoss et al. . |
| 5,614,414 | 3/1997 | Ryan et al. . |

FOREIGN PATENT DOCUMENTS

| | | |
|---|---|---|
| 0118634 | 9/1984 | European Pat. Off. . |
| 0311035 | 4/1989 | European Pat. Off. . |
| 0433516 | 6/1991 | European Pat. Off. . |
| 0469766 | 2/1992 | European Pat. Off. . |
| 2114291 | 8/1984 | United Kingdom . |
| WO 91/17436 | 11/1991 | WIPO . |
| WO 92/19951 | 11/1991 | WIPO . |
| WO 94/06290 | 3/1994 | WIPO . |

OTHER PUBLICATIONS

Sigma Chemical Catalog p. 1379, 703, 1987.
De Grost et al, Contact Dermatitis 18:202–205, 1988.
Perret et al Arch. Dermatol. Res. 281(1):57–59, 1989.
Berk et al, Cosmetics & Toiletries, 97(6):49–53, 1982.
McCarthy, D.A. et al., "A Simple Flow Cytometric Procedure for the Determination of Surface Antigens on Unfixed Leucocytes in Whole Blood," *J. Immunol. Meth.* 163:155–160 (1993).
Eachus, K. et al., "Nitroparafin–Derived Heterocyclic Antimicrobial Compounds," *SOFW* 9:337–342 (1991).
Tome, Y. et al., Preservation of cluster 1 small cell lung cancer antigen in zinc–formalin fixative and its application to immunohistological diagnosis, *Histopathal.* 16:469–474 (1990).
Jones, M.J. et al., Laboratory Investigations 44:32A (1981).
"Cosmetics and Drug Preservation," Kobava, J. ed., pp. 177–178, 647 and 657–659.
Histochoice™ Tissue Fixative, Clinical Lab Products (1992).
Product data sheet: TB47 Angus.
Product data sheet: TB54 Angus.
Product data sheet: TDS10 Angus.

(List continued on next page.)

*Primary Examiner*—Nita Minnfield
*Attorney, Agent, or Firm*—Harness, Dickey & Pierce, P.L.C.

[57] ABSTRACT

A method and composition for fixing and stabilizing tissues, cells, and cell components such that the antigenic sites and nucleic acids are preserved is provided. The fixative employs a formaldehyde donor that is non-toxic, non-flammable, and that stabilizes the cell with minimal damage to and alteration of the cell morphology. The cell antigenic sites are left intact so that studies with monoclonal antibodies may be conducted. Vaccines and related immunotherapeutic methods utilizing antigens stabilized by the fixative of the present invention are also provided. Also disclosed is a method for developing a positive control for test reagents and for test instrumentation.

25 Claims, 5 Drawing Sheets

OTHER PUBLICATIONS

Product data sheet: TDS28 Angus.
Product data sheet: TDS30 Angus.
Product data sheet: TDS40 Angus.
Product data sheet: TDS41 Angus.
Product data sheet: HULS.

Product data sheet: HULS Nuosept 65.

Product data sheet: HULS Neusept 95.

Product data sheet: HULS Nuosept 145.

Keran, "Flow Cytometry in Clinical Diagnosis," pp. 311–330 (1989).

METHOD AND COMPOSITION FOR PRESERVING ANTIGENS AND NUCLEIC ACIDS AND PROCESS FOR UTILIZING CYTOLOGICAL MATERIAL PRODUCED BY SAME

RELATED APPLICATIONS

The present application is a continuation-in-part of U.S. Ser. No. 08/603,740, filed 20 Feb. 1996, which is a divisional of U.S. Ser. No. 08/240,404, filed 10 May 1994 now abandoned, which claims priority under 35 U.S.C. §120 from PCT International Application No. PCT/US93/08520, filed 9 Sep. 1993, which is a continuation-in-part of U.S. Ser. No. 07/943,359, filed 10 Sep. 1992, now abandoned, which is a continuation-in-part of U.S. Ser. No. 07/877,738, filed 4 May 1992, now U.S. Pat. No. 5,260,048, and a continuation-in-part of U.S. Ser. No. 07/696,926, filed 8 May 1991, now U.S. Pat. No. 5,196,182.

The present application is also related to the following applications: PCT International Application PCT/US92/03758, filed 8 May 1992, naming Wayne L. Ryan as inventor, and designating the Contracting States of the European Patent Convention and Japan; U.S. Ser. No. 08/048,711, filed 16 Apr. 1993, now abandoned; U.S. Ser. No. 08/233,223, filed 26 Apr. 1994, now U.S. Pat. No. 5,459,073; U.S. Ser. No. 08/333,875, filed 3 Nov. 1994, now U.S. Pat. No. 5,460,797, which is a continuation of U.S. Ser. No. 08/052,648, filed 26 Apr. 1993, now abandoned.

Each of the foregoing listed applications is hereby incorporated by reference in its entirety.

FIELD OF THE INVENTION

The present invention generally relates to compositions useful for the stabilization and fixation of cells and tissues and, more particularly, to compositions for the stabilization and fixation of cells and tissues that preserve antigenic sites and nucleic acids for a useful period of time. The present invention also describes a process for stabilizing the antigenic sites and nucleic acids of cells or cell components. The present invention further describes processes for utilizing cells or cell components for use in histological, cytological, immunological, and proteinaceous studies, and the like. Also disclosed, as a further aspect of the invention, is a vaccine preparation and immunotherapeutic methods utilizing the stabilization and fixation compositions of the present invention.

BACKGROUND OF THE INVENTION

In biological and biochemical analysis, and related arts, it is often necessary to store and preserve biological tissues, such as cells, cell components, proteins, and certain organic components thereof, for useful periods of time. Such biological materials are often utilized in a wide variety of applications, including, but not limited to, instructional aids and the diagnosis and treatment of diseases. For example, certain organisms and components thereof are often preserved in or by solutions for use in the learning arts. Likewise, such biological materials are often utilized in histological, cytological, oncological, genetic, virological, hematological, immunological, and proteinaceous studies, and the like.

Because of their accessibility, white blood cells are often used in many diagnostic procedures. For example, quantification of $CD4^+$ antigens on the white blood cell surface is diagnostic for HIV infection; the nucleic acids of the cells are analyzed to find genetic errors and for typing prior to tissue transplantation; and alterations in white blood cells are diagnostic for many types of cancer.

The techniques employed in analyzing the components of white blood cells require a high level of technology that is usually found in larger laboratories and samples, therefore, are routinely shipped to the larger laboratories. In addition, these laboratories may wish to store samples until a sufficient quantity of samples are collected to make analyzing a batch of samples economical. Because unstabilized white blood cells have, at the most, 24 to 48 hour stability, they must be stabilized. Unfortunately, current formulations for stabilization of cells contain one or more agents which react vigorously with the proteins of the cells to denature and insolubilize the components of the cell. For example, compounds typically used to stabilize cells may preserve some cellular antigens though certain antigens are more sensitive and lose reactivity. Examples of such antigens are the CD antigens present on the surface of hematopoietic cells. Because much of the clinically useful applications of surface marker analysis, and much of the development of the surface marker assay technology, has focused on lymphocyte CD markers, it would be desirable to provide a formulation which stabilizes white blood cells without losing CD antigen reactivity.

Another problem with the use of existing compounds which stabilize cells for analysis is that certain critical antigens are present in small quantities and thus become undetectable, even if only a small percentage of these antigens are destroyed. The known formulations are, therefore, not useful when cellular detail is required.

The toxicity associated with known formulations for stabilization of cells also renders their use less than satisfactory. For example, the most common fixative, formaldehyde, most commonly employed as a 37 percent aqueous solution, is a noxious gas which is also toxic, flammable, and carcinogenic. Although efforts are made when this chemical is used to protect workers and avoid contamination of the drainage system when disposed of, these efforts are usually both expensive and inconvenient, and, despite such efforts, fixatives such as formaldehyde still present a danger to laboratory workers and health care professionals. Thus, it is also desirable to develop fixatives which can be used safely, effectively and conveniently in histological studies.

The AIDS virus also poses a threat to laboratory workers, with clinical laboratory personnel accounting for twenty percent of all cases of occupationally transmitted HIV in the United States. Thus, it is also desirable to reduce laboratory workers' risk of exposure to HIV by developing fixatives which kill cell-associated HIV in tissue samples from persons with HIV infection.

Various methods known in the art for analyzing histological, cytological, immunological, and proteinaceous materials utilize flow cytometry to evaluate cellular properties. Flow cytometry and flow cytometers are generally described in Keren's text, *Flow Cytometry in Clinical Diagnosis* (1989). Flow cytometers operate in principle by multiparameter analysis of heterogeneous cell populations (or cellular components) on a cell-by-cell basis. Flow cytometry allows biological and physical properties of cells and cellular components to be determined.

In flow cytometry, cells in suspension are forced single file, via hydrodynamic focusing, through the path of a laser beam. Interaction of the cells with the laser beam scatters some of the light and causes excitation and emission from fluorescent molecules present on the surface or interior of the cell. A series of lenses collects the scattered and/or emitted light and passes it to a photomultiplier. Each photomultiplier measures a separate parameter. Parameters measured include: forward light scatter, which measures relative particle size; side light scatter, which measures relative granularity or other internal structure; and fluorescence emission. The optical signals are converted by a computer to a data display for analysis and interpretation.

A chromophore may be applied to a cell suspension or the cells may be labeled with monoclonal antibodies which have been conjugated directly or indirectly with fluorochromes. These probes are usually specific for a surface antigen or some intracellular substance of interest, such as DNA. The choice of the probe depends on the diagnostic or biological parameter of clinical interest.

Therefore, it is an object of the invention to provide a fixative solution for tissues and cells which has an extremely low toxicity, yet meets all of the requirements of a model fixative.

Another object of the invention is to provide a fixative solution for tissues and cells that preserves tissues and cells and their cellular detail and, in particular, does not alter cell surface antigens, cytoplasmic antigens, RNA or DNA.

Another object of the present invention is to provide a fixative which, in addition to being low in toxicity, gives off no noxious fumes, is not flammable or carcinogenic, and which can be disposed of more safely and conveniently than fixatives known in the art.

Yet another object of the invention is to provide a fixative solution for tissues and cells that preserves tissues and cells and their antigenic detail to allow for the satisfactory conducting of immunohistochemical and other immunological techniques on the tissues and cells.

Yet another object of the invention is to provide a fixative solution that provides an unaltered antigenic surface for reaction with specific antibodies for use, for example, in the preparation of vaccines and in related immunotherapeutic methods.

Yet another object of the invention is to provide cytological controls for use in biological analysis and studies.

Yet another object of the invention is to provide methods to stabilize blood cell components, in particular white blood cells, without damaging the white blood cell antigens and nucleic acids. Such stabilization would permit shipping stabilized samples to distant sites for analysis and/or storage of stabilized samples until sufficient number of samples are collected for analysis on site.

Yet another object of the invention is to provide a fixative solution that kills cell-associated HIV (preferably within 48 hours) while preserving the viral RNA.

These and other objects of the invention are obtained by a fixative solution for tissues and cells comprising a histological fixing amount of at least one active agent selected from the group consisting of:
i) diazolidinyl urea,
ii) imidazolidinyl urea,
iii) dimethylol-5,5-dimethylhydantoin,
iv) dimethylol urea,
v) 2-bromo-2-nitropropane-1,3-diol,
vi) 5-hydroxymethoxymethyl-1-aza-3,7-dioxabicyclo[3.3.0]octane and 5-hydroxymethyl-1-aza-3,7-dioxabicyclo[3.3.0]octane and 5-hydroxypoly[methyleneoxy]methyl-1-aza-3,7-dioxabicyclo[3.3.0]octane, and
vii) sodium hydroxymethyl glycinate.

In another aspect, the invention comprises an improved method of fixing tissues and cells with a histological fixative, the improvement comprising the use of a fixative solution which comprises a histological fixing amount of at least one active agent selected from the group consisting of:
i) diazolidinyl urea,
ii) imidazolidinyl urea,
iii) dimethylol-5,5-dimethylhydantoin,
iv) dimethylol urea,
v) 2-bromo-2-nitropropane-1,3-diol,
vi) 5-hydroxymethoxymethyl-1-aza-3,7-dioxabicyclo[3.3.0]octane and 5-hydroxymethyl-1-aza-3,7-dioxabicyclo[3.3.0]octane and 5-hydroxypoly[methyleneoxy]methyl-1-aza-3,7-dioxabicyclo[3.3.0]octane, and
vii) sodium hydroxymethyl glycinate.

A preferred fixative solution for tissues and cells comprises a histological fixing amount of at least one of the following active agents:
i) diazolidinyl urea, and
ii) imidazolidinyl urea.

A highly preferred fixative solution of the present invention comprises imidazolidinyl urea (IDU), polyethylene glycol and EDTA, preferably in a buffered physiological salt solution. The preferred buffered salt solution is phosphate buffered saline, however magnesium gluconate-sodium citrate buffered saline, tissue culture media such as RPMI, or other biological buffers known in the art may also be employed. The preferred concentration of IDU is from about 4% to about 6% by weight, and most preferably about 5% by weight. The preferred concentration of polyethylene glycol is up to about 1% by weight and the most preferred concentration is about 0.5% by weight. The preferred concentration of EDTA is up to about 0.2% by weight and the most preferred concentration is about 0.1% by weight. The preferred pH of the fixative solution of the present invention is from about 6.0 to about 8.0, and 7.25 is most preferred. The preferred osmolarity is from about 250 mosm to about 450 mosm and 375 mosm is most preferred. The preferred fixative solution may also include protease inhibitors such as AEBSF and/or lysine.

An additional highly preferred fixative solution of the present invention comprises Du, preferably in a buffered physiological salt solution. The preferred buffered salt solution is phosphate buffered saline, however, magnesium gluconate-sodium citrate buffered saline, tissue culture media such as RPMI, other known biological buffers known in the art may also be employed. The preferred concentration of Du is from about 1% to about 20% by weight, and most preferably, about 10% by weight. The preferred pH of this fixative solution containing Du is from about 6.6 to about 7.6, and 7.25 is most preferred. The preferred osmolarity is from about 500 mosm to about 750 mosm, and 650 mosm is most preferred. The preferred Du containing fixative solution may also include protease inhibitors such as AEBSF and/or lysine.

In another highly preferred embodiment of the present invention, the method of preserving the tissue sample employs both Du and IDU. The tissue can be contacted sequentially with a Du containing fixative solution and an IDU containing fixative solution or with a single solution containing both Du and IDU. When a sample is to be contacted with Du and IDU sequentially, it is preferable to contact the cells with Du first, followed by contacting with IDU. When the fixative of the present invention contains a mixture of Du and IDU, the preferred total concentration of Du plus IDU is from about 4% to about 10% by weight, most preferably from about 6% to about 7% by weight, at a ratio of Du to IDU from about 10:1 to about 1:10, preferably from about 1:1 to about 1:10, and most preferably about 1:4.

When the tissue sample to be fixed is peripheral blood, bone marrow, lymph node, spleen or umbilical cord, it is preferred to treat the samples by direct mixing with the fixative solution of the present invention. The preferred volume ration of sample to reagent is from about 1:4 to about 2:1, with 1:1 being the most preferred.

Unlike the typical histological fixing agents, the active agents of the present invention have extremely low toxicity. For example, toxicity studies comparing diazolidinyl urea of the invention with formaldehyde of the prior art show the following:

|  | Inhalation Toxicity | Dermal Toxicity | LD50 |
| --- | --- | --- | --- |
| Formaldehyde | 500 mg/kg | 270 mg/kg | 800 mg/kg |
| Diazolidinyl urea | None | 2000 mg/kg | 2570 mg/kg |

This reduced toxicity makes disposal and handling less of a problem. In addition, since there is no inhalation toxicity, there are no badge detection devices required as there are for formaldehyde. Another advantage offered by the active agents of the invention is that they are not flammable and therefore do not present a fire hazard as do many of the prior art fixatives.

The mechanism by which the active agents of the present invention preserve antigens is not fully understood, however, it is most likely due to the reaction between protein and the active agents of the invention. For example, known preservatives, such as formaldehyde, cross-link with itself and proteins to obscure the antigen. To determine if this is true, a preferred active agent of the present invention, diazolidinyl urea, was added to the protein albumin. After incubation of the diazolidinyl urea and protein mixture for 24 hours, disc-gel electrophoresis indicated no change in the rate of migration of the protein. In contrast, when this experiment was conducted with formaldehyde, a large number of multimers and insoluble proteins resulted. Moreover, although the active agents of the present invention are known to be formaldehyde donors, it is known that the small amount of formaldehyde held in equilibrium with the reagent is not the active mechanism of the instant compositions, i.e., when compounds which react readily with the free formaldehyde are added, for example, glycine, allantoin, and sulfites, the tissue fixation still occurs.

In another aspect of the invention, it has been found that the addition of alkali metal salts of ascorbic acid increases the activity of the active agents of the invention in fixing the tissue or cell membrane.

In yet another aspect of the invention, it has been found that the addition of glycine, or other formaldehyde reactive compounds, is useful in removing any free formaldehyde which may be an equilibrium component of the compositions of the instant invention. It should be noted, however, that the preferred compositions of the instant invention contain only trace amounts of formaldehyde in equilibrium.

In yet a further aspect of the invention, it should be understood that biological material fixed or stabilized by the composition and method of the instant invention need not be stored in the composition, but may be fixed or stabilized and subsequently stored in an alternative environment.

It should be noted that the process for fixing biological material described in the instant specification may be practiced by those skilled in the art to preserve antigenic sites and nucleic acids of cells (or components thereof) derived from any source including normal blood, bone marrow, lymph, or solid tissues, or may be derived from abnormal tissues such as leukemias or solid tissue cancers. The present invention may also be utilized with any cellular component or biological material which has at least one antigenic site.

In yet a further aspect of the present invention, it has been found that the fixative of the present invention may be used in the preparation of vaccines and in related immunotherapeutic methods. Thus, a vaccine comprising an antigen treated with the fixative of the present invention, in a biologically compatible form suitable for administration in vivo, and methods of administering the same to a recipient in an amount sufficient to enhance the immune response, is also provided by the present invention. Furthermore, it has been found that in vivo administration of the fixative of the present invention produces an effective immunogen, and thus a method of "boosting" an in vivo immune response in a recipient by administering the fixative of the present invention in a biologically compatible form suitable for administration in vivo, in an amount sufficient to enhance the immune response, is also provided by the present invention. By "biologically compatible form suitable for administration in vivo" is meant a form to be administered in which the toxic effects, if any, are outweighed by the therapeutic effects of the immunotherapy. Moreover, administration can be in any suitable pharmacological form, which includes, but is not limited to, intravenous injection.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE INVENTION

Figure 1:
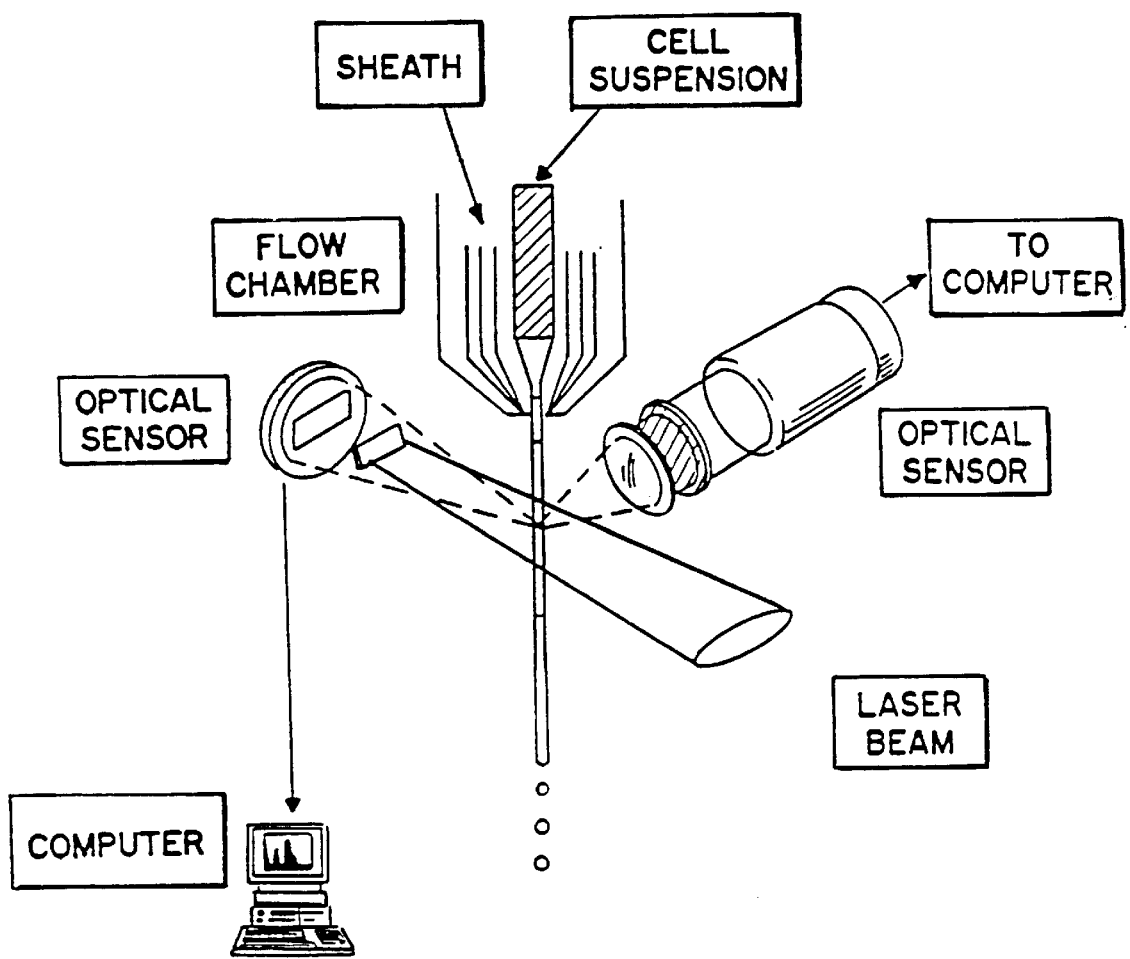
FIG. 1 is a schematic diagram of a flow cytometer.
Figure 2:
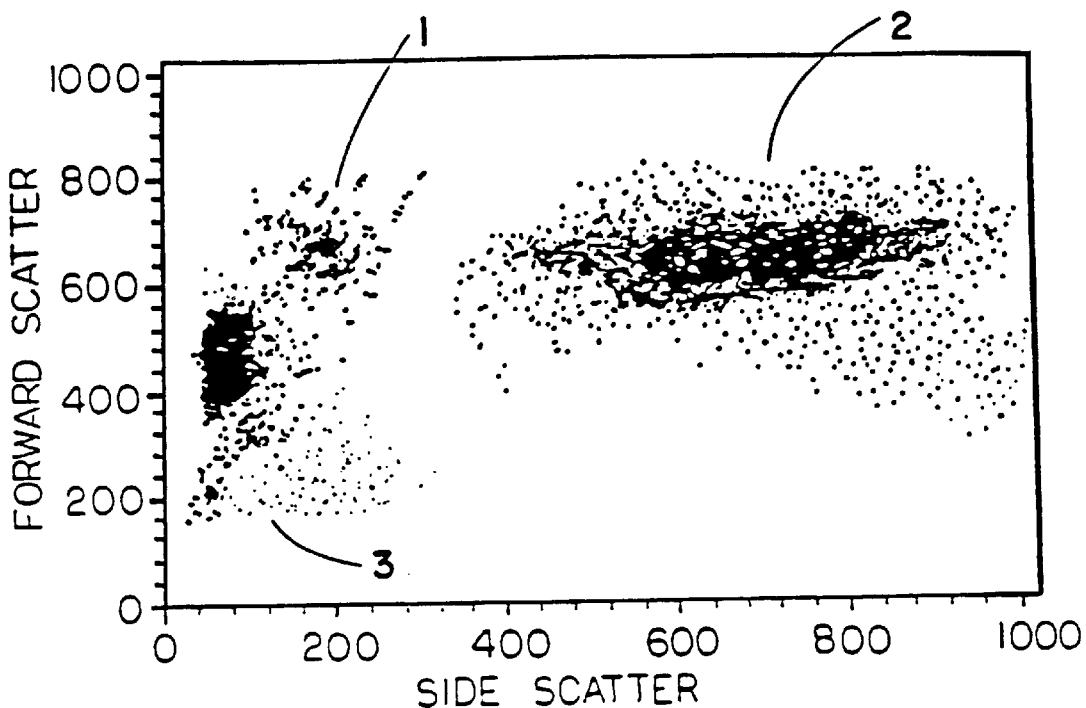
FIG. 2 is a graphical illustration of a flow cytometry scattergram wherein the enumeration of subsets is given, and wherein monocytes 1, granulocytes 2, and lymphocytes 3 are illustrated.
Figure 3:
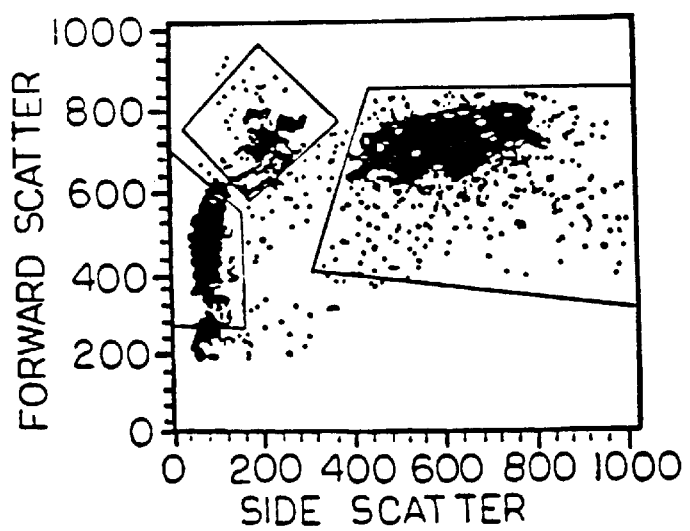
FIG. 3 is a graphical illustration of the same scattergram as illustrated in FIG. 2 wherein the subsets are "gated;"
Figure 4A:
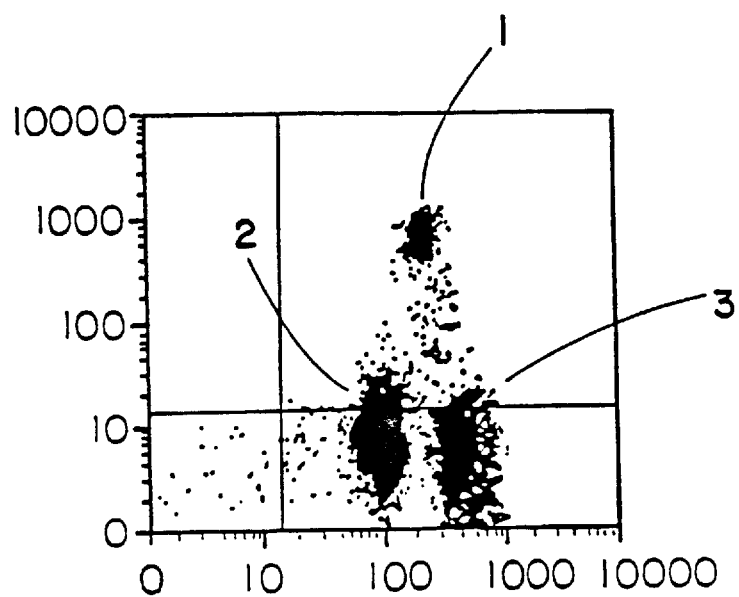
FIGS. 4A and 4B are graphical illustrations of dot plots wherein phenotyping of subsets was accomplished by means of fluorescence.
Figure 4B:
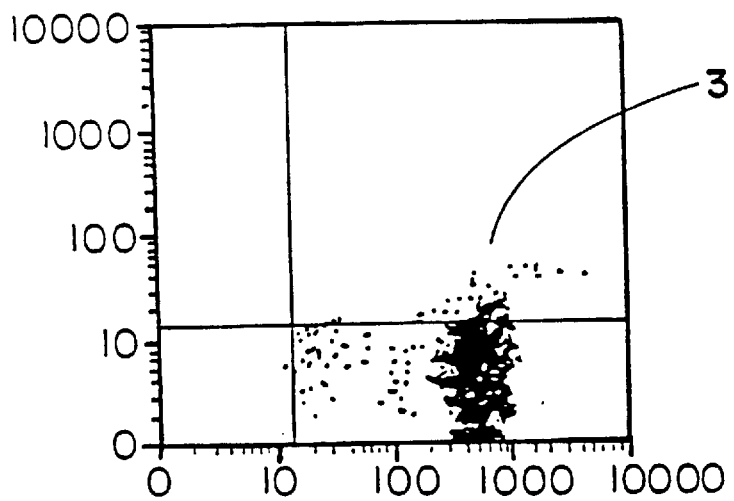
Figure 5:
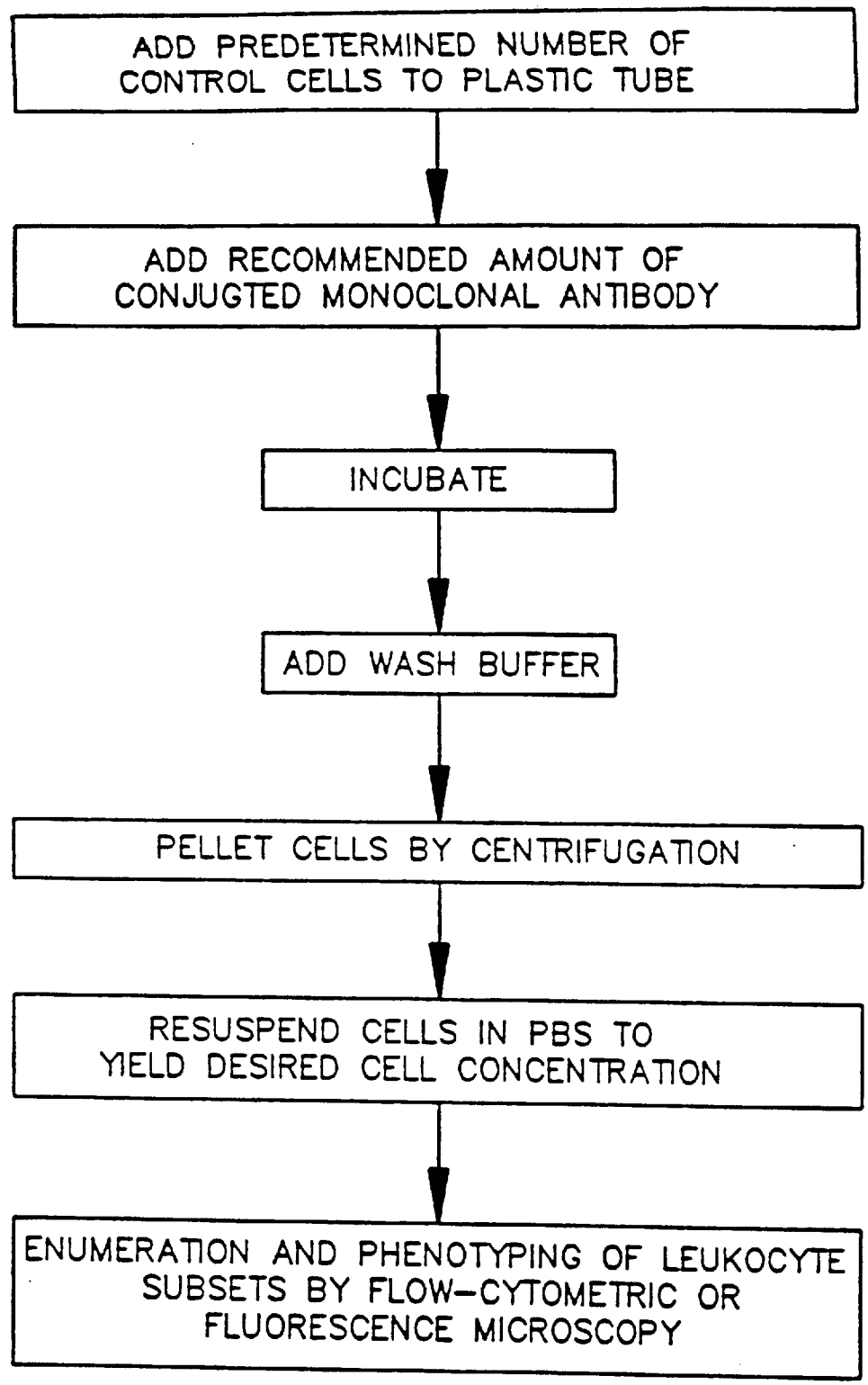
FIG. 5 is a flow diagram illustrating the procedure for preparing stabilized leukocytes for antigen-antibody studies.
Figure 6:
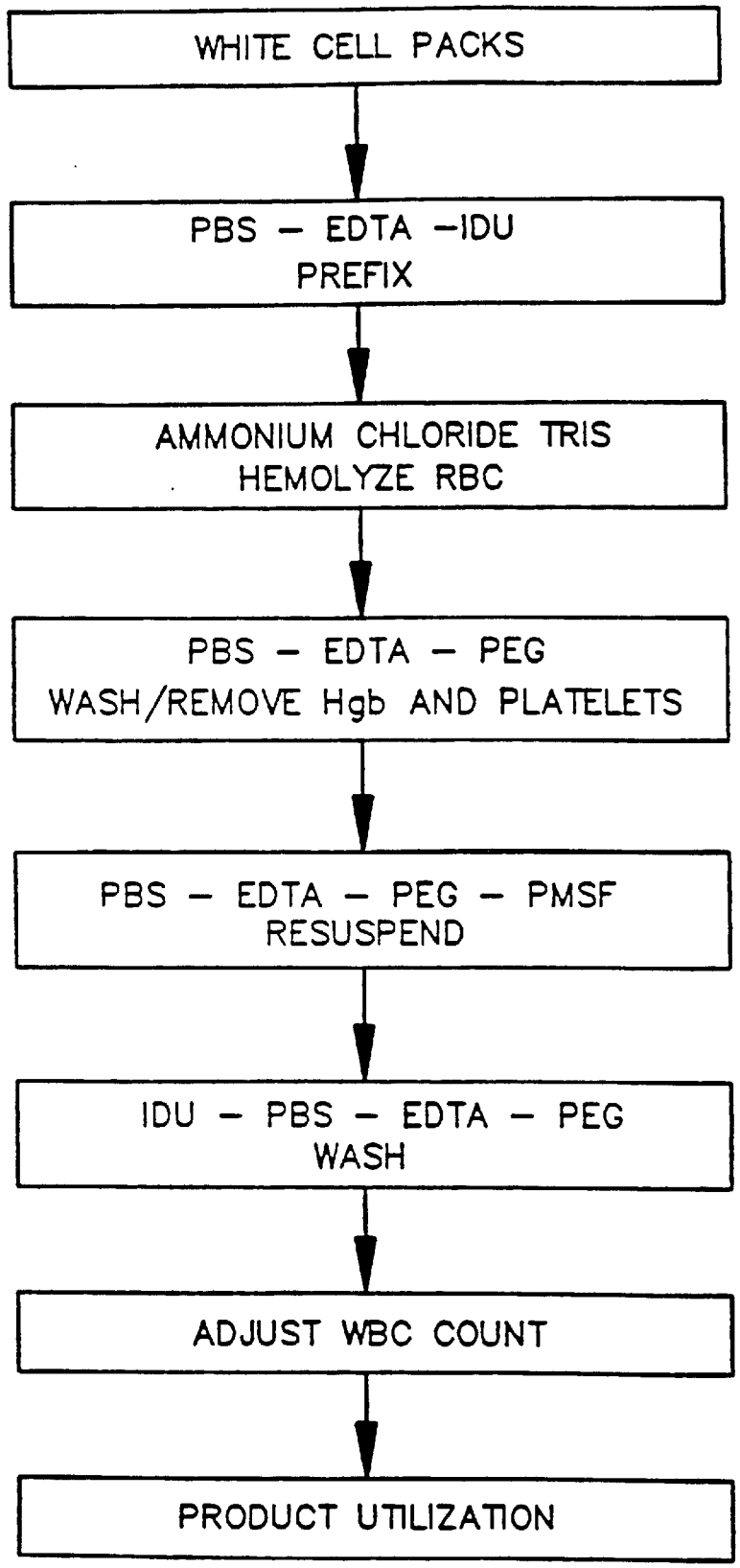
FIG. 6 is a flow diagram illustrating the procedure for preparing stabilized leukocyte subsets as a control.

Fixative solutions and methods for fixing and stabilizing cells and tissues are provided. The fixative solutions of the present invention may be used to fix or stabilize cells and tissues while preserving antigenic sites and nucleic acids of the cells, tissues and components thereof. In a preferred embodiment, the fixative solutions are employed to fix or stabilize white blood cells and, in particular, to fix or stabilize white blood cells without damaging the cluster designation (CD) antigens on the surface of the white blood cells and/or the intracellular and extracellular nucleic acids of the white blood cells. The fixative solutions and methods of the present invention are therefore useful in fixing or stabilizing white blood cells which are later used in diagnostic applications such as, for example, quantifying CD4+ antigens in diagnosing HIV infection and analyzing nucleic acids for identifying genetic errors and typing prior to tissue transplantation.

The fixative solutions of the present invention generally comprise an active agent in solution. Suitable solvents include water, saline, dimethylsulfoxide, alcohol, and mixtures thereof. In a preferred embodiment of the present invention, the fixative solution comprises diazolidinyl urea (Du) and/or imidazolidinyl urea (IDU) in a buffered physiological salt solution. In a highly preferred embodiment, the fixative solution further comprises polyethylene glycol and EDTA.

The alcohol solvent of the present invention generally comprises one or more alkanols and/or polyols. Suitable alkanols include straight or branched chain alkanols having 1–4 carbons, such as methanol, ethanol, propanol, and butanol. Suitable polyols include diols and triols, such as ethylene glycol, propylene glycol, trimethylene glycol, and glycerol.

In another preferred embodiment of the present invention, a suitable buffer such as a citrate buffer may be added to the solution to adjust the pH to about 4 to about 6. One particularly preferred citrate buffer to be used in the solution is sodium citrate dihydrate, but other buffers may be utilized as would be obvious to one skilled in the art.

Whether the solvent employed is water, alcohol, dimethylsulfoxide, or a mixture thereof, depends principally upon the tissue or cells being fixed. For example, where large pieces of tissue are being fixed, it is preferable to use an alcohol solvent or aqueous alcohol solvent since the alcohol solvents increase penetration. Also, in fixing cells such as Pap smears, the alcoholic preparations are preferred because they cause the cells to adhere to slides. When aqueous alcoholic solutions are employed as the solvent for the active agents of the invention, the ratio of alcohol to water will fall approximately in the range of 4:1 to 2:1.

The amount of the active agents in the formulation of the invention is that effective to fix or stabilize the tissue or cell membrane. Generally, this amount falls in the range of about 10 to about 200 grams per liter. In a preferred embodiment, the fixative solutions comprise about 4 to about 6 grams of IDU per 100 ml of buffered salt solution and/or about 1 to about 20 grams of Du per 100 ml of buffered salt solution.

The solute in the preparations of the invention may also include any additional components conventionally found in histological fixative preparations. These include, without limitation, mordants, buffers, penetration increasers, osmotically active substances, nuclear detail improvers, and nuclear size increasers. Examples of suitable mordants are salt of a metal having an oxidation state of two or more, e.g., zinc, strontium, calcium, barium, and chromium salts. The preferred salt is zinc sulfate. Suitable buffers include alkali metal phosphate salts, such as sodium phosphate and potassium phosphate. Osmotically active substances that may be included in the formulation of the invention are alkali metal salts, such as sodium chloride. In addition, sugars, such as the polysaccharides, sucrose, glucose, and the like, may be employed. Nuclear detail improvers and nuclear size increasers include acetic acid and lithium salts such as lithium chloride. Zinc salts, such as zinc sulfate, not only improve nuclear definition, but also improve staining. Illustrative of substances which increase the rate of penetration of the fixing agent are dimethylsulfoxide and ethanol.

The fixative solutions of the present invention may be used in a number of applications as would be known to one skilled in the art. For example, the fixative solution may be used to preserve samples of tissues that are being shipped or carried to an examination site. In this process, small vials or jars that have liquid tight seals are filled with the reagent of the invention, and tissue samples are placed in the reagent-filled container to preserve the samples until they reach an area where further processing can occur. Specific Example I sets forth an exemplary protocol for this method.

Tissues prepared for study using the fixative of the invention may be prepared for histological study in any known manner, such as through the use of paraffin sectioning equipment, staining, mounting on slides, or other common steps utilized prior to microscopic or other examination. The present invention thus provides a safe, convenient and effective fixative solution which may be utilized in the many known histological procedures that employ fixative solutions.

The fixatives of the present invention may also be used in the preparation of vaccines. Virus and toxin vaccines, for example, which are currently prepared with formaldehyde, may be prepared by employing the fixatives of the present invention. Due to the ability of the active agents of the present invention to preserve antigen integrity, vaccines employing antigens stabilized with the active agents of the present invention provide an enhanced immune response compared to antigen stabilization with currently known fixatives. It has also been shown that the active agents of the present invention may be used as an immunogen in vivo to enhance an immune response.

The following example illustrates a preferred embodiment of the present invention.

SPECIFIC EXAMPLE I

Patient samples are treated by mixing them directly with a preferred fixative solution of the present invention. The preferred ratio of sample to reagent is 1:1 but a ratio as low as 1:4 or as high as 2:1 is acceptable. For example, 1 ml peripheral blood is added to a vial containing 1 ml fixative solution, mixed and stored at 4° C. for up to seven days. White blood cells may be analyzed by flow cytometry for the presence of cell surface antigens, cytoplasmic antigens, DNA content or specific nucleic acid sequences by polymerase chain reaction (PCR) or in situ hybridization using established protocols, e.g., U.S. Pat. No. 5,225,326 entitled "One Step In Situ Hybridization Assay," specifically incorporated by reference herein. Samples treated with the preferred fixative solution of the present invention are compatible with standard RBC lysing agents such as FACSllyse® or Q-Prep® as well as density gradient methods using such products as Histopaque®-1077.

Samples may be diluted to stabilize human blood cells up to seven days for subsequent analysis by flow cytometry. The following exemplary protocol may be employed. Collect blood samples into $K_3$ EDTA vacutainer by venipuncture and mix. Add 1 ml sample to vial containing 1 ml preferred fixative solution. Invert vial by hand 3 times to mix. Store sample vial at 2°–8° C. for 0–7 days until use. Mix sample vial thoroughly by hand inversion, at least 25 times. Aliquot 100 µl sample into analysis tubes. Incubate with monoclonal antibody according to manufacturer's directions. Process sample with red blood cell lyse/fix reagents according to manufacturer's directions. Wash sample one time with flow cytometry analysis buffer routinely used and known to those skilled in the art. Suspend in 0.5 ml flow cytometry analysis buffer and analyze by flow cytometry.

An additional reagent fixative solution preferably used to preserve nucleic acids may also be prepared by adding 10% diazolidinyl urea (Du) to phosphate buffered saline, pH 7.3. This reagent is diluted 1:1 with cell suspensions to produce a final concentration of 5% Du WN. The use of Du provides more rapid and greater stabilization of the cells than IDU. It is usually employed when cells are intended for use in nucleic acid analysis by in situ hybridization or PCR techniques. These procedures require some harsh treatments such as heating to 50° C. or more to anneal the nucleic acids and treatment with surfactants to permeabilize the cells. If the cells are fixed inadequately, the sample cannot be used for flow cytometry or microscopy. The use of Du preserves the cell structure, nucleic acids, and cell antigens. Thus, the sample can be transported or held in the lab for several days. Furthermore, when the tissue sample contains HIV, the compositions of the present invention kill cell-associated HIV within 48 hours, thus reducing the risk of exposure and infection by laboratory workers. Formaldehyde and similar fixatives do not provide acceptable results. For example, U.S. Pat. No. 5,225,326, herein incorporated by reference, describes a number of fixatives commonly used for in situ hybridization (see col. 4, line 23). Types of cells that may be used include: cord blood, venous blood, bone marrow, epithelial ovarian cancer, lymph node, and cervical cells.

For example, epithelial ovarian cancer cells contained in peritoneal fluid aspirated from ovarian cancer patients can be treated with the Du containing fixative solution of the present invention. Subsequently, the cells may be analyzed by in situ hybridization for the presence of oncogenes such as HERZ/neu and fms or tumor suppressor genes such as p53. Identification of the genetic characteristics of the epithelial ovarian cancer cells would aid the physician in selecting the best course of treatment for each patient.

SPECIFIC EXAMPLE II

The following example is illustrative of several formulations of the fixative solutions of the present invention.

| A) | Diazolidinyl urea | 50 g |
| --- | --- | --- |
|  | $Na_2HPO$ | 0.73 g |
|  | $KHPO_4$ | 0.02 g |
|  | NaCl | 8.50 g |
|  | Distilled $H_2O$ to one liter |  |
| B) | Diazolidinyl urea | 50 g |
|  | Ethanol | 500 ml |
|  | Acetic acid, conc. | 10 ml |
|  | Distilled $H_2O$ to one liter |  |
| C) | Diazolidinyl urea | 50 g |
|  | Lithium chloride | 6.35 g |
|  | Distilled $H_2O$ to one liter |  |
| D) | Diazolidinyl urea | 50 g |
|  | Dimethylsulfoxide | 100 ml |
|  | Distilled $H_2O$ to one liter |  |
| E) | Diazolidinyl urea | 50 g |
|  | Dimethylsulfoxide | 100 ml |
|  | Zinc chloride | 5.8 g |
|  | Distilled $H_2O$ to one liter |  |
| F) | Diazolidinyl urea | 50 g |
|  | Ascorbic acid, sodium | 0.25 g |
|  | Distilled $H_2O$ to one liter |  |

SPECIFIC EXAMPLE III

The following is an example of a use of the fixative solutions of the present invention.

Tissue is immersed in one of the fixative solutions described in Specific Examples I and II for four hours. The treated tissue is then dehydrated through a series of graded alcohols, cleared in xylene and impregnated with molten paraffin. This procedure is performed under heat and vacuum/pressure in a 12-hour cycle using a Fisher Histomatic (Model 166 MP) tissue processor. The tissue is then blocked, paraffin embedded, rehydrated in ice water for a minimum of three hours to enhance sectioning, and sectioned at 4–5 microns. The tissue is mounted on a glass slide, deparaffinized, stained, coverslipped and evaluated microscopically.

SPECIFIC EXAMPLE IV

The following examples demonstrates the satisfactory results obtained with the fixative of the invention using various staining methods.

Example III was repeated using the staining method identified below. The results in each case are as follows:

| Staining Method | Results |
| --- | --- |
| Mayer's mucicarmine | Demonstrable; well defined |
| Elastin | Satisfactory detail |
| Movat's reticulin stain | Satisfactory detail; minimal shrinkage |
| Gomori's trichrome stain | Fibrous tissue well defined |
| Periodic Acid-Schiff (PAS) | Non-specific staining not evidenced as in formalin-fixed preparation |
| Geimsa | Satisfactory detail |
| Hematoxylin & eosin (H&E) | Satisfactory detail |

SPECIFIC EXAMPLE V

The following example demonstrates the ability of the fixative solution of the present invention in retaining tissue antigens in immunostaining procedures.

The tissues identified below having the antigenic sites identified below were fixed with the fixative formulation of Specific Example II A) and immunohistochemically stained using avidin-biotin staining.

| Tissue | Markers Detected |
| --- | --- |
| Lymph node | LN-1; LN-2; LN 3; UCA; L-26; LCHL-1 |
| Brain | Neurofilament; Glial Fibrillary Acidic Protein |
| Hodgkins node | Ber $H_2$; Leu $M_1$ |
| Colon | Cytokeratin MAK-6; Cytokeratin AE1/AE3 |
| Muscle | Desmin |
| Pituitary | S-100 |
| Breast | α-lactalbumin |
| Thyroid | Thyroglobulin |

SPECIFIC EXAMPLE VI

A fixative solution in accordance with the present invention was prepared having the following formulation: 30 grams of Bronopol; 30 grams of diazolidinyl urea; 12 grams of zinc sulfate heptahydrate; and 2.9 grams of sodium citrate dihydrate dissolved in 1000 ml distilled water. This solution was used as a fixative for tissue samples by placing the samples in a vial containing the fixative solution, and holding the sample for about four hours in the fixative. After the tissue was sufficiently treated with fixative, it was then dehydrated using a series of graded alcohols, cleared in xylene and impregnated with molten paraffin. This procedure was performed under heat and vacuum/pressure in a 12-hour cycle using a Fisher Histomatic (Model 166MP) tissue processor. The tissue was then blocked, paraffin embedded, rehydrated in ice water for about three hours to enhance sectioning, and sectioned at 4–5 microns. The tissue was mounted on a glass slide, deparaffinized, stained, coverslipped and evaluated microscopically.

Through use of the composition and method of the present invention, satisfactory results have been obtained with a variety of staining methods. The following results were obtained using the fixative of the invention:

| Staining Method | Results |
| --- | --- |
| Mayer's mucicarmine | Demonstrable; well defined |
| Elastin | Satisfactory detail |
| Movat's reticulin stain | Satisfactory detail; minimal shrinkage |
| Gomori's trichrome stain | Fibrous tissue well defined |
| Periodic Acid-Schiff (PAS) | Non-specific staining not evidenced as in formalin-fixed preparation |
| Hematoxylin & eosin (H&E) | Satisfactory detail |
| Geimsa | Satisfactory detail |

SPECIFIC EXAMPLE VII

The tissues identified below having the antigenic sites identified below were fixed with the fixative formulation of Specific Example VI and immunohistochemically stained using avidin-biotin staining.

| Tissue | Markers Detected |
| --- | --- |
| Lymph node | LN-1; LN-2; LN-3; LCA; L-26; UCHL-1; B72.3 |
| Brain | Neurofilament; Glial Fibrillary Acidic Protein; Vimentin |
| Hodgkin's node | Ber $H_2$; Leu $M_1$ |
| Muscle | Desmin; Smooth Muscle Actin |
| Pituitary | S-100 |
| Thyroid | Throglobulin |
| Breast | α-lactalbumin; Estrogen Receptors (ER's); Progesterone Receptors (PR's) |
| Skin | HMB 45 Melanoma |
| Colon | Cytokeratin MAK-6; Cytokeratin AE1/AE3; Epithelial Membrane Ag (EMA) |

None of the antigenic sites were affected by the immunostaining.

SPECIFIC EXAMPLE VIII

The following example describes a leukocyte positive control check for antigen-antibody studies.

Positive control methods are needed to verify the performance of reagents, preparation methods, staining procedures as well as the performance of the flow cytometer instrumentation itself. This requires a preparation of human white blood cells, preferably with a mixed distribution of leukocytes (lymphocytes, monocytes, and granulocytes), to evaluate the performance of the procedure before it is used to evaluate subject tissues, cells, or cell components. While much of the methodology used in this procedure is familiar to those skilled in the art, this invention is novel in its use of IDU as a cell stabilizer, the use of polyethylene glycol to reduce damage to the white blood cells during processing, the use of PMSF to inhibit protease activity, and the process itself.

The invention discloses a new method of producing a positive control check material with significant advances over the prior art. Production is begun by placing one pack of human white blood cells, obtainable from commercial blood banks, in each bottle of the centrifuge. Samples from each pack are placed into a plastic tube for screening on the flow cytometer. Because of the considerable variation from donor to donor in cluster designation antigen sites, only packs with similar properties are pooled. Each product pool should be limited to a particular ABO blood type to prevent clumping as a result of a histo-incompatibility reaction between the cells. The samples are placed into plastic tubes rather than glass because unfixed white blood cells may be activated by the glass causing them to adhere to the glass and each other.

The cells are prefixed 1:1 with 1% IDU in phosphate buffered saline ethylenediaminetetraacetic acid (PBS-EDTA) at 6° C. for one hour. This acts to stabilize the white blood cells without interfering with the lysis of the red blood cells. The cells and all diluents used in the processing must be kept at 6° C. at all times by use of refrigeration and a chiller bath to reduce the amount of cell damage which alters the scattergram.

The bottles are next centrifuged at 900 rpm for 10 minutes, and the supernatant is removed. This angular velocity is sufficient to pellet the white blood cells without damaging them. Ammonium chloride tris, 200 ml/bottle set at 6° C. for 20–30 minutes, is then used to lyse the red blood cells.

A second centrifugation follows, again at 900 rpm for 10 minutes and then the supernatant is removed. Next 250 ml/bottle of ammonium chloride tris are added at 6° C. or 45–60 minutes, with 60 minutes usually ensuring complete lysis of the red blood cells.

The material is then centrifuged a third time at 900 rpm for 10 minutes and then the supernatant is removed. If the cell pellets still contain red blood cells, add 150 ml/bottle of ammonium chloride tris at 6° C. for 20 to 30 minutes and centrifuge a fourth time at 900 rpm for 10 minutes and remove the supernatant.

The cells are then washed three times with PBS/EDTA/1% polyethylene glycol (PEG) 20,000 by centrifuging at 900 rpm for 10 minutes and removing the supernatant.

After the final wash, each bottle is resuspended with 100 ml of PBS/EDTA/0.3% PEG/3% IDU/2mM phenylmethylsulfonyl fluoride (PMSF) and set at 6° C. for 2 days. Fixation with 3% IDU stabilizes the cells for use on the flow cytometer, with lower concentrations of IDU reducing stability and higher concentrations causing cells to lose the cluster designation marker and produce scatterplot changes. Next each bottle is washed two times with PBS/EDTA/0.3% PEG/3% IDU to remove PMSF and residual platelets.

Finally, the white blood cell count of each bottle selected for final pooling should be adjusted to meet the final product specifications. These counts may be performed on the ELT 1500 or ZBI, in triplicate, prior to pooling.

The product is now ready for use in aiding laboratory studies in that a desired reagent may be combined with the product and then examined with a flow cytometer to establish a normal baseline for the evaluation of subject tissue, cells, and cell components.

The product prepared according to this procedure may be utilized to analyze more antibodies since it contains lymphocytes, monocytes, and granulocytes. Thus, the product of this process is more complete control and all WBC's produce a scattergram similar to that of whole blood.

Product produced by the before mentioned procedure has a seven day open vial stability, does not have to be reconstituted, is compatible with all major flow cytometry systems, and one product may be utilized to monitor several areas of quality control.

The present invention has several advantages over prior art controls. For example, the prior art controls: (1) do not resemble human specimens, i.e., size, shape and granularity; (2) have short open vial stability (24 hours); (3) are lyophilized and must be reconstituted; and (4) cannot be utilized to test lyse procedures.

SPECIFIC EXAMPLE IX

The following example describes methods for staining cell surfaces.

The indirect method of immunofluorescence staining of cell surfaces may be used to enhance the fluorescence signal, and may also be utilized with the present invention to enhance its function as a positive control check. Since indirect methods will alter the proportionality between the amount of antigen and the fluorescence intensity per cell, these methods are not recommended for assessing the absolute number of antigenic determinants per cell, but are effective in determining the relative quantitative differences between control and subject cell populations.

Direct immunofluorescence staining of cell surfaces is used to detect cells bearing specific membrane antigens by treating a cell population with monoclonal antibodies conjugated to fluorescein or phycoerythrin, and is recommended for analysis by flow cytometry or fluorescence microscopy. The use of the present invention control procedure is ideally suited to the direct immunofluorescence staining method in establishing a quality control program for laboratory reagents, procedures, and flow cytometers.

SPECIFIC EXAMPLE X

The following example describes a method of immunotherapy utilizing the fixative solutions of the present invention.

Tumor specific antigens appear labile and antigens must be presented to the immune system while on the tumor cell. Thus, studies to determine whether tumor cells could be stabilized by the fixative of the present invention to produce an effective tumor specific antigen were performed.

6C3HED lymphosarcoma (obtained from NCI) was grown in C3H mice (purchased from Jackson Labs) as ascites (ascites cause collection of fluid in the peritoneal cavity and death in about 18–21 days). The ascites cells were then washed in phosphate buffered saline (PBS) containing 3% IDU or 3% Glydant or 3% Dimethylol urea. It will be appreciated by those skilled in the art that any appropriate diluent such as water may also be used. The cells were then placed at 6° C. for 48 hours. Vital staining indicated that none of the cells were viable. The tumor cells stabilized with the above fixatives can be stored for at least four months without loss of effectiveness as a vaccine.

As a control for immunization, cells were then washed into PBS containing 3% para formaldehyde and held under the same conditions. After 48 hours, all the cell groups were washed into PBS to remove the fixatives. The cell count was adjusted to 200,000/ml. Five C3H mice were injected intraperitoneally with 2–5×$10^5$ cells of each of the cell groups for the first immunization. The procedure was repeated two weeks later.

The immunized mice were challenged with 2×$10^6$ viable 63HED ascites cells by intraperitoneal injection. The efficacy of the immunization was determined by the average death time for each group of mice.

| | Average Death Days | |
|---|---|---|
| A. | Control | 18 days |
| B. | IDU | No deaths at 65 days |
| C. | Glydant | No deaths at 65 days |
| D. | Dimethylol urea | No deaths at 65 days |

This experiment was repeated several times with variations in timing and dosage. In every instance the immunized mice survived (100%) and the control mice died (100%).

To determine if a therapeutic response can be obtained, the mice were also injected with the tumor challenge, i.e. 2×$10^6$ viable 63HED ascites cells, first and then immunized later. By using this protocol, it was possible to protect 50% of the mice, i.e., 50% of the mice lived. The mice that were immunized and died lived an average of 40 days (death usually occurs at 18–21 days). It is thus evident that even under these circumstances, protection is conferred.

The possible effect of IDU on tumor cells in vivo was also studied. Live tumor cells were injected intraperitoneally into the mice. After three days, an intraperitoneal injection of IDU was given. This was repeated two more times at three day intervals.

At 7.5 mg/mouse IDU, all of the untreated (control) mice died. 30% of the treated mice survived. The average death time for the treated mice that died was 41 days. At 15 mg/mouse IDU, all of the control mice died. The treated mice all survived and small tumors developed which regressed in about two to three days. At 30 mg/mouse IDU, all of the control mice died and all of the treated mice survived. The treated mice were also held for three months to determine if the tumor would recur. No tumors appeared. Based on these findings, it is believed that the IDU is binding with the tumor cells in vivo to produce an effective immunogen.

Studies utilizing tetanus toxin treated with the fixative of the present invention were also performed. Tetanus toxin must be treated before it can be used to immunize and presently this is done with formalin. In order to compare formalin and the fixative of the present invention, Swiss mice were inoculated intraperitoneally with tetanus toxin prepared by inactivation with IDU or formalin. Although the level of IDU used can be 1% or greater, for this experiment, a 5% solution (final) was used to inactivate the toxin. The antibody levels were then measured at 14 and 28 days.

| | 14 Days | 28 Days |
|---|---|---|
| IDU | 200 | 560 |

These values set forth the percent increase in antibody titer over formalin.

It should be noted that the concentration range for the active ingredient is best established in order to preserve antigenic sites by setting a low-end which preserves the cell or protein and also preserves the physical properties of cell size and granularity. The upper-end is set so as to preserve the antigenic sites and provide reproducible results over time.

SPECIFIC EXAMPLE XI

A 6% w/v solution of each of the compounds listed below was used and samples tested at 24 hours (22° C.) for red blood cell (RBC) and white blood cell (WBC) fixation.

Relative RBC fixation was detected by adding known RBC lysing agent. WBC's were detected as fixed if these cells did not disintegrate or clump over a period of approximately two hours after removal of the compound.

1) Bronopol: 2-bromo-2-nitropropane-1,3-diol. Synthesized from p-formaldehyde and nitromethane, then bromated. Decomposition liberates formaldehyde. Fixes both RBC's and WBC's.
2) Imidazolidinyl urea: Synthesized by reaction of allantoin and formaldehyde. Decomposition releases formaldehyde. Fixes both RBC's and WBC's.
3) Diazolidinyl urea: Synthesized by reaction of allantoin and formaldehyde. Contains 1–2 ppm of formaldehyde. Fixes both RBC's and WBC's.
4) Glydant: Dimethylol-5,5-dimethylhydantoin, a formaldehyde derivative. solution contains 2.1% formaldehyde. Fixes both RBC's and WBC's.
5) Dimethylol urea: Synthesized from urea and formaldehyde. Formaldehyde is released in very small quantities. Fixes both RBC's and WBC's.
6) NUOSEPT® 95: Sold by Huls America, Inc., Piscataway, N.J. Contains:
   a) 5-hydroxymethoxymethyl-1-aza-3,7-dioxabicyclo [3.3.0]octane,
   b) 5-hydroxymethyl-1-aza-3,7-dioxabicyclo[3.3.0] octane,
   c) 5-hydroxypoly[methyleneoxy]methyl-1-aza-3,7-dioxabicyclo [3.3.0]octane.
   Fixes both RBC's and WBC's.
7) Suttocide: Sodium hydroxymethyl glycinate. Derivative of glycine. Fixes both RBC's and WBC's. Contains 1% formaldehyde.

SPECIFIC EXAMPLE XII

Over 30 peripheral blood samples from healthy donors were collected by venipuncture into ETDA vacutainers and were analyzed both before and during a seven day treatment with the fixative solution according to the present invention containing 50 g IDU, 8.15 g NaCl, 0.73 g $Na_2HPO_4$, 0.02 g $KH_2PO_4$, 1.0 g $Na_2EDTA$, 5.0 g PEG 20,000, and distilled water to 1 liter. One ml blood was added to one ml fixative, inverted 3 times to mix and stored at 6° C. until analysis. At each time point, a 100 µl aliquot of cells was reacted with 5 µl each of FITC- and PE-conjugated monoclonal antibodies. For example, 5 µl CD3-FITC and 5 µl CD-19-PE; 5 µl CD3-FITC and 5 µl CD4-PE. After 20 minutes incubation at room temperature in the dark, samples were treated with 2 ml FACSlyse for 10 more minutes to lyse the red blood cells. Then, samples were centrifuged at 200 r.c.f. for 5 minutes, washed two times with 1 ml PBS buffer containing 0.5% BSA and 0.9% $NaN_3$ (sodium azide) and analyzed on a Becton-Dickinson FACScan flow cytometer using Simulset software. Lymphocytes were gated using CD45-FITC and CD14-PE. Background staining was evaluated using isotype control monoclonal antibodies. Representative immunophenotyping data from five patient samples is shown below. In all cases, WBC subsets enumerated by immunophenotyping blood treated with the fixative solution of the present invention do not differ from WBC subsets in the initial untreated sample.

|  | CD3% | CD19% | CD4% | CD8% | CD16+56% | CD4:CD8 | Lymph % |
|---|---|---|---|---|---|---|---|
| Donor 1 | | | | | | | |
| Day 0 | 87 | 7 | 56 | 31 | 6 | 1.81 | 21 |
| Day 3 | 86 | 7 | 55 | 33 | 5 | 1.67 | 23 |
| Day 5 | 88 | 7 | 57 | 33 | 6 | 1.73 | 23 |
| Day 7 | 88 | 6 | 56 | 31 | 6 | 1.81 | 26 |
| Donor 2 | | | | | | | |
| Day 0 | 70 | 13 | 48 | 21 | 15 | 2.29 | 22 |
| Day 3 | 71 | 13 | 48 | 23 | 17 | 2.09 | 25 |
| Day 5 | 78 | 12 | 48 | 22 | 15 | 2.18 | 25 |
| Day 7 | 80 | 12 | 50 | 23 | n/a | 2.17 | 24 |
| Donor 3 | | | | | | | |
| Day 0 | 81 | 9 | 55 | 24 | 7 | 2.29 | 30 |
| Day 3 | 82 | 9 | 57 | 24 | 8 | 2.38 | 32 |
| Day 5 | 83 | 8 | 57 | 24 | 9 | 2.38 | 35 |
| Day 7 | 80 | 6 | 61 | 24 | 8 | 2.54 | 32 |
| Donor 4 | | | | | | | |
| Day 0 | 75 | 12 | 41 | 32 | 10 | 1.28 | 32 |
| Day 3 | 76 | 13 | 41 | 33 | 9 | 1.24 | 32 |
| Day 5 | 76 | 13 | 41 | 33 | 9 | 1.24 | 34 |
| Day 7 | 79 | 13 | 42 | 31 | 9 | 1.35 | 31 |
| Donor 5 | | | | | | | |
| Day 0 | 75 | 15 | 51 | 28 | 7 | 1.8 | 21 |
| Day 3 | 74 | 17 | 48 | 27 | 7 | 1.8 | 22 |
| Day 5 | 75 | 14 | 49 | 29 | 7 | 1.7 | 23 |
| Day 7 | 77 | 15 | 48 | 28 | 5 | 1.7 | 19 |

SPECIFIC EXAMPLE XIII

Over 100 peripheral blood samples from AIDS patients were collected by venipuncture into ETDA vacutainers and were analyzed both before and after a four day treatment with the Du containing fixative of the present invention containing 50 g IDU, 8.15 g NaCl, 0.73 g $Na_2HPO_4$, 0.02 g $KH_2PO_4$, 1.0 g $Na_2EDTA$, 5.0 g PEG 20,000, and distilled water to one liter. The procedure of Specific Example XII was followed except that the samples were lysed with Q-Prep and analyzed on a Coulter Epics Elite flow cytometer using Epics Elite version 4.0 software. Representative immunophenotyping data from six patient samples is shown below. In all cases, WBC subsets enumerated by immunophenotyping blood treated with the fixative solution of the present invention do not differ from WBC subsets in the initial untreated sample.

|  | CD3% | CD4% | CD3% | CD8% | CD4:CD8 |
|---|---|---|---|---|---|
| Donor 1 | | | | | |
| Day 0 | 46 | 2 | 42 | 37 | 0.06 |
| Day 4 | 48 | 2 | 47 | 41 | 0.05 |
| Donor 2 | | | | | |
| Day 0 | 92 | 9 | 90 | 77 | 0.12 |
| Day 4 | 88 | 10 | 92 | 83 | 0.12 |
| Donor 3 | | | | | |
| Day 0 | 69 | 1 | 68 | 65 | 0.01 |
| Day 4 | 73 | 1 | 72 | 70 | 0.01 |
| Donor 4 | | | | | |
| Day 0 | 84 | 13 | 80 | 59 | 0.22 |
| Day 4 | 84 | 15 | 83 | 67 | 0.22 |
| Donor 5 | | | | | |
| Day 0 | 81 | 26 | 80 | 51 | 0.51 |
| Day 4 | 85 | 28 | 83 | 55 | 0.51 |
| Donor 6 | | | | | |
| Day 0 | 82 | 7 | 81 | 71 | 0.10 |
| Day 4 | 82 | 6 | 87 | 79 | 0.08 |
| Donor 7 | | | | | |
| Day 0 | 70 | 24 | 70 | 39 | 0.63 |
| Day 4 | 74 | 25 | 71 | 42 | 0.60 |
| Donor 8 | | | | | |
| Day 0 | 87 | 5 | 86 | 78 | 0.07 |
| Day 4 | 87 | 5 | 85 | 78 | 0.06 |
| Donor 9 | | | | | |
| Day 0 | 79 | 25 | 81 | 52 | 0.47 |
| Day 4 | 84 | 24 | 81 | 58 | 0.41 |

SPECIFIC EXAMPLE XIV

Cocultivation assays were performed to determine HIV-1 virus inhibition. The composition of the present invention containing 5% Du in PBS was added to MT-4 cells infected with HIV-1 virus. The cells were incubated for 4 hours at 22° C. The Du was then removed by washing and the treated infected cells were added to a fresh culture of MT-4 cells (cocultivation). The presence of infectious HIV-1 was monitored by immunofluorescence for capsid protein (P24) and envelope protein (GP120) at biweekly intervals for up to 29 days. At day 4, the untreated control cells show 95% positive for virus. In the Du treated group, no infected cells were observed. The above process was repeated, except that a 3% solution of IDU in PBS, according to the present invention was employed. The 3% IDU decreased viral infectivity so that it took the treated cells 12–18 days to infect the fresh culture, but did not completely kill all virus.

The use of 1% paraformaldehyde in the above test system produced no active virus after 4 and 24 hour incubation. Studies by Ericson et al. with a similar system indicated that incubation for 1 hour in 1% paraformaldehyde was inadequate to significantly reduce the infectivity of HIV-1 and that incubation for 42 hours in 2% paraformaldehyde was necessary.

All of the disinfectants described above as cell fixatives or stabilizers may be used to fix cells or tissues. The concentration and additives ($ZnSO_4$, ethylene glycol, etc.) will vary depending upon the circumstances of use. The characteristics common to all of the above disinfectant compounds are that they contain formaldehyde as an equilibrium component, they can be synthesized from formaldehyde, they are chemical disinfectants, they are capable of undergoing hydrogen bonding, and they function to fix or stabilize at concentrations two to ten times their usual concentration as a bactericide.

SPECIFIC EXAMPLE XV

A bone marrow aspirate from a patient was collected aseptically into a sterilized heparinized container and mixed well. The sample was analyzed both before and during a four day treatment with the fixative solution according to the present invention containing 50 g IDU, 8.15 g NaCl, 0.73 g $Na_2HPO_4$, 0.02 g $KH_2PO_4$, 1.0 g $Na_2EDTA$, 5.0 g PEG 20,000, and distilled water to 1 liter. One ml marrow was added to one ml of fixative, mixed well, and stored at 6° C. until analysis. At each time point, a 100 µl aliquot of cells was reacted with 5 µl each of FITC- and PE-conjugated monoclonal antibodies, e.g., 5 µl CD3-FITC and 5 µl CD19-PE; 5 µl CD3-FITC and 5 µl CD4-PE. After 20 minutes incubation at room temperature in the dark, samples were treated with 2 ml lyse for 10 more minutes to lyse the red blood cells. Then samples were centrifuged at 200 r.c.f. for 5 minutes, washed two times with 1 ml PBS buffer and analyzed on a Coulter XL system. Lymphocytes were gated using CD45-FITC and CD14-PE. Background staining was evaluated using isotype control monoclonal antibodies. The results demonstrate WBC subset stability of bone marrow treated with the fixative solution of the present invention.

|  | Day 0 | Day 2 | Day 3 | Day 4 |
|---|---|---|---|---|
| CD2% | 68 | 70 | 66 | 65 |
| CD3% | 60 | 62 | 63 | 63 |
| CD4% | 40 | 38 | 40 | 36 |
| CD5% | 56 | 54 | 52 | 52 |
| CD7% | 59 | 60 | 57 | 58 |
| CD8% | 18 | 20 | 18 | 18 |
| CD10% | 2 | 1 | 2 | 0 |
| CD14% | 1 | 0 | 1 | 1 |
| CD20% | 22 | 20 | 20 | 18 |
| HLA/DR% | 72 | 70 | 68 | 70 |
| CD19% | 25 | 22 | 20 | 22 |
| Kappa% | 18 | 20 | 17 | 17 |
| Lambda% | 6 | 5 | 8 | 7 |
| Glycol% | 24 | 20 | 23 | 25 |
| CD56% | 10 | 10 | 8 | 8 |

Whereas the invention has been described in connection with preferred embodiments and procedures thereof, it is apparent that many additions, modifications and substitutions may be made which are within the intended broad scope of the appended claims. Thus, there has been shown and described an improved composition, method, and process which accomplishes at least all of the stated objects.

All patents and other references cited herein are expressly incorporated by reference.

I claim:

1. A method of preserving a tissue sample having one or more antigenic sites, comprising suspending said tissue sample in a solution comprising a fixative in an amount sufficient to preserve the antigenic sites, wherein said fixative is selected from the group consisting of imidazolidinyl urea, diazolidinyl urea, and mixtures thereof.

2. The method of claim 1, wherein the antigenic sites include cluster designation markers.

3. The method of claim 2, wherein said antigenic sites include $CD4^+$ antigenic sites.

4. The method of claim 1, wherein the solution comprises from about 4 to about 6 percent by weight imidazolidinyl urea.

5. The method of claim 4, wherein the solution comprises about 5 percent by weight imidazolidinyl urea.

6. The method of claim 1, wherein the solution further comprises phosphate buffered saline.

7. The method of claim 1, wherein the solution further comprises an additive selected from the group consisting of ethylenediaminetetraacetic acid, polyethylene glycol, and mixtures thereof.

8. The method of claim 7, wherein the solution further comprises about 0.001 to about 0.2 percent by weight ethylenediaminetetraacetic acid.

9. The method of claim 7, wherein the solution comprises up to about 1 percent by weight polyethylene glycol.

10. The method of claim 1, wherein the solution comprises a mixture of imidazolidinyl urea and diazolidinyl urea.

11. The method of claim 10, wherein the solution comprises a total concentration of imidazolidinyl urea and diazolidinyl urea from about 4 percent to about 10 percent by weight wherein the weight ratio of imidazolidinyl urea to diazolidinyl urea is from about 10:1 to about 1:10.

12. The method of claim 1, wherein the tissue sample is selected from the group consisting of normal peripheral blood, bone marrow, lymph node, spleen, umbilical cord, and solid tissues.

13. The method of claim 1, wherein the tissue sample is an abnormal tissue sample selected from the group consisting of leukemias and solid tissue cancer.

14. A method of preserving a tissue sample having one or more nucleic acids comprising suspending said tissue sample in a solution comprising a fixative in an amount sufficient to preserve said nucleic acids, wherein said fixative is selected from the group consisting of imidazolidinyl urea, diazolidinyl urea, and mixtures thereof.

15. The method of claim 14, wherein the nucleic acid is RNA.

16. The method of claim 15, wherein the nucleic acid is viral RNA.

17. The method of claim 16, wherein the nucleic acid is HIV RNA.

18. The method of claim 14, wherein the nucleic acid is DNA.

19. The method of claim 14, wherein the solution comprises from about 1 to about 20 percent by weight diazolidinyl urea.

20. The method of claim 19, wherein the solution comprises about 10 percent by weight diazolidinyl urea.

21. The method of claim 14, wherein the solution further comprises phosphate buffered saline.

22. The method of claim 14, wherein the solution comprises a mixture of imidazolidinyl urea and diazolidinyl urea.

23. The method of claim 22, wherein the solution comprises a total concentration of diazolidinyl urea and imidazolidinyl urea from about 4 percent to about 10 percent by weight wherein the weight ratio of diazolidinyl urea to imidazolidinyl urea is from about 1:1 to about 1:10.

24. The method of claim 14, wherein the tissue sample is selected from the group consisting of normal peripheral blood, bone marrow, lymph node, spleen, umbilical cord, and solid tissues.

25. The method of claim 14, wherein the tissue sample is an abnormal tissue sample from the group consisting of leukemias and solid tissue cancers.

* * * * *